United States Patent
Greco et al.

(10) Patent No.: US 11,969,489 B2
(45) Date of Patent: Apr. 30, 2024

(54) MELTING MASSAGE BAR

(71) Applicant: Johnson & Johnson Consumer Inc., Skillman, NJ (US)

(72) Inventors: Joseph Greco, Skillman, NJ (US); Jessica Maciejewski, Skillman, NJ (US); Alexandria Dinapoli Marzano, Skillman, NJ (US); MaryRose Wagner, Ambler, PA (US)

(73) Assignee: JOHNSON & JOHNSON CONSUMER INC., Skillman, NJ (US)

( * ) Notice: Subject to any disclaimer, the term of this patent is extended or adjusted under 35 U.S.C. 154(b) by 0 days.

(21) Appl. No.: 17/173,400

(22) Filed: Feb. 11, 2021

(65) Prior Publication Data

US 2021/0244628 A1    Aug. 12, 2021

Related U.S. Application Data

(60) Provisional application No. 62/972,797, filed on Feb. 11, 2020.

(51) Int. Cl.
| | |
|---|---|
| *A61K 8/02* | (2006.01) |
| *A61K 8/34* | (2006.01) |
| *A61K 8/92* | (2006.01) |
| *A61Q 19/00* | (2006.01) |

(52) U.S. Cl.
CPC ............ *A61K 8/0216* (2013.01); *A61K 8/342* (2013.01); *A61K 8/922* (2013.01); *A61K 8/927* (2013.01); *A61Q 19/007* (2013.01); *A61K 2800/805* (2013.01)

(58) Field of Classification Search
CPC ..... A61K 8/0216; A61K 8/922; A61Q 19/007
See application file for complete search history.

(56) References Cited

U.S. PATENT DOCUMENTS

| | | | | |
|---|---|---|---|---|
| 9,561,173 B2 * | 2/2017 | Constantine | ......... | A61K 8/0233 |
| 9,884,005 B2 | 2/2018 | Ambrosen et al. | | |
| 10,111,826 B2 | 10/2018 | Constantine et al. | | |
| 2005/0123574 A1 * | 6/2005 | Abbas | .................. | C11D 17/06 |
| | | | | 424/70.22 |
| 2009/0082239 A1 * | 3/2009 | Baquete | ................ | C11D 3/373 |
| | | | | 510/144 |
| 2018/0185268 A1 | 7/2018 | Frushour et al. | | |

FOREIGN PATENT DOCUMENTS

WO    WO 2014/179305 A1    11/2014

OTHER PUBLICATIONS

Mintel "Solid Conditioner Boho Bar" (Oct. 9, 2019, GNPD Database No. 6926125; provided by Applicant) (Year: 2019).*
Mintel "Solid Conditioner" (Jun. 7, 2019, GNPD Database No. 6604773; provided by Applicant) (Year: 2019).*
Jan. 16, 2019, Society of Cosmetic Chemists. "What Is the Stratum Corneum and Its Importance in Skin Care?" Cosmetics Business, 2016, www.cosmeticsbusiness.com/news/article_page/What_is_the_stratum_corneum_and_its_importance_in_skin_care/143839.
Gunstone, F. D. Fatty Acid and Lipid Chemistry. Springer, Dec. 6, 2012 (Book). https://books.google.com/books/about/Fatty_Acid_and_Lipid_Chemistry.html?id=QYUpBAAAQBAJ.
Lencki, Robert W., and R. John Craven. "Negative Pressure Induced Cavity Formation During Cocoa Butter Crystallization." SpringerLink, Springer Berlin Heidelberg, Jul. 3, 2013, link.springer.com/article/10.1007%2Fs11746-013-2294-0.
Karagounis et al., Use of "natural" oils for moisturization: Review of olive, coconut, and sunflower seed oil, Pediatric Dermatology, 2019;36:9-15.
Lin et al., Anti-Inflammatory and Skin Barrier Repair Effects of Topical Application of Some Plant Oils, Int. J. Mol. Sci. 2018, 19, 70.
Cizinauskas et al., Fatty acids penetration into human skin ex vivo: ATOF-SIMS analysis approach, Biointerphases 12(1), Mar. 2017.
International Search Report; PCT/IB2021/051129; dated May 18, 2021.
Mintel: "Solid Conditioner," XP055801094, Database accession No. 6604773; dated Jun. 7, 2019.
Mintel: "Solid Conditioner Boho Bar," XP055801099, Database accession No. 6926125, dated Oct. 9, 2019.
Mintel: "Frangipani Flowers Solid Body Oil," XP055801090; Database accession No. 4102973, dated Jun. 30, 2016.
Mintel: "Ultra Rich Cream Wash," XP055801086; Database accession No. 3158217, dated May 12, 2015.
Lush USA; Mintel: "Melt and Massage Bars," Record ID 10192111; dated Oct. 2004 https://www.lushusa.com/body/massage-bars.
Kate Mcleod Inc.; Body Stones; Mintel: "CBD Stone," Record ID: 7134867; dated Jan. 2020; www.katemcleod.com.
https://cosdna.com/chs/cosmetic_cc09372809.html; Jun. 20, 2018; Palmer's Cocoa Butter Formula, Body Lotion, Massage Lotion for Stretch Marks, 8.5 fl oz (250 ml) Palmer's, Cocoa Butter.

* cited by examiner

*Primary Examiner* — Andrew S Rosenthal
(74) *Attorney, Agent, or Firm* — Samuel J. Gee

(57) ABSTRACT

A personal care cosmetic composition; its method of manufacture; and its method of use are disclosed.

9 Claims, 1 Drawing Sheet

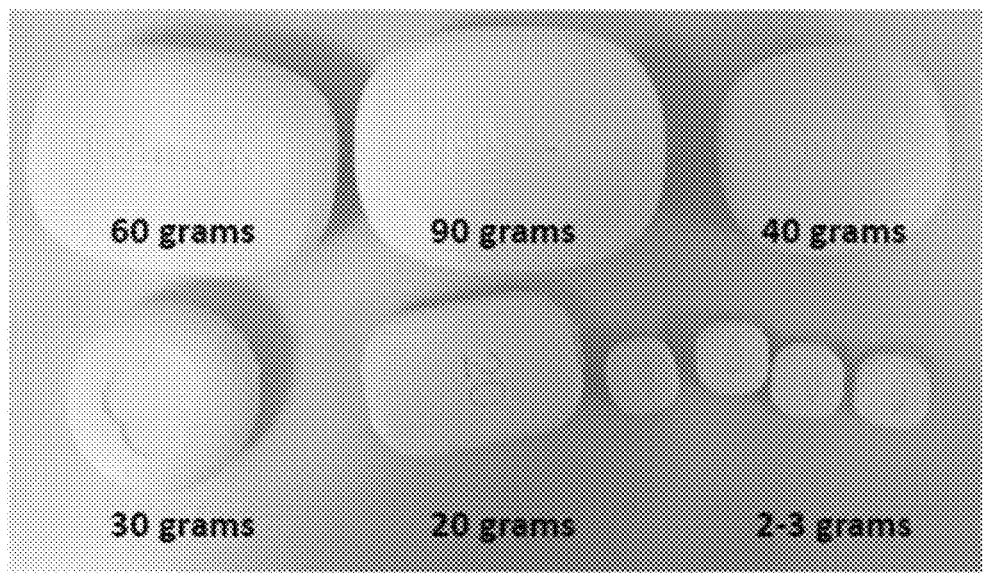

MELTING MASSAGE BAR

FIELD OF THE INVENTION

The present invention relates to products particularly those for use in contact with the human body.

BACKGROUND OF THE INVENTION

Consumers, who are becoming more aware of where the products they buy come from and of the social and environmental challenges being faced by the developing and developed world, are in search of ways to minimize their impact. One aspect of ethical buying has been to change packaging to tackle the plastic problem. Another has been to formulate with more "natural" ingredients.

A cosmetic product which has been increasingly popular is massage bars. These products contain a solidified oil or fat molded into a product which may be held easily in the hand. Alternatively, a larger sized product may be made from which a small piece may be broken and then used. In use, the massage bar is applied to the skin of the recipient either as a complete bar or by breaking off a small piece of product which is then applied to the skin. These solid products are both popular for home use and for application by a professional masseur.

For home use, a single solid product which may be applied many times is often considered to be acceptable. However for professional use, for example by a masseur or in a spa, multiple use of a single product is not acceptable. For reasons of hygiene it is not acceptable for one product to be used on one recipient and then later used on a different recipient. This problem may be addressed by use of small pieces of product broken from a larger piece or by providing as small single use size samples.

Kate Mcleod Inc. markets and sells BODY STONES full-body moisturizers. See www.katemcleod.com. The site discloses that all of their BODY STONES are made using the same five core ingredients, i.e., cocoa butter, sweet almond oil, apricot kernel oil, avocado oil, and fractionated coconut oil. The listed price of the product is $45. The present inventors tested this product and found that although it had a nice glide, it did not melt fast enough.

Lush USA discloses massage bars. See https://www.lush-usa.com/body/massage-bars. The site discloses that its Hottie bar contains the following ingredients: Fair Trade Organic Cocoa Butter (*Theobroma cacao*), Shea Butter (*Butyrospermum parkii*), Cold Pressed Organic Jojoba Oil (*Simmondsia chinensis*) (Cold Pressed Organic Jojoba Oil (*Simmondsia Chinensis*)), Fragrance, Ginger Oil (*Zingiber Officinale*), Vanilla Absolute (*Vanilla planifolia*), Black Pepper Oil (*Piper nigrum*), *Benzyl Salicylate, *Citral, *Coumarin, *Geraniol, *Benzyl Benzoate, *Benzyl Cinnamate, *Farnesol, Butylphenyl Methylpropional, *Limonene, and *Linalool. The listed price of the product is $12-14. The present inventors tested this product and found that although it had a nice melt profile, the product was too oily on skin.

U.S. Pat. No. 9,561,173 to Cosmetic Warrior, Inc. discloses a solid cosmetic composition that includes (i) an outer layer having (a) a hard vegetable butter in an amount of 10 to 45 wt. % based on the outer layer, and (b) a soft vegetable butter in an amount of 55 to 80 wt. % based on the outer layer. The composition also includes an (ii) inner core which is (a) a soft vegetable butter composition; (b) a fondant; or (c) a liquid cosmetic.

U.S. Pat. Nos. 9,884,005 and 10,111,826 to Cosmetic Warrior, Inc. discloses a solid cosmetic composition having dispersed therein gas bubbles, and a process for making a solid cosmetic composition.

It is desired to have a product with the following aesthetic profile:
  Feel in hand: dry, not sticky, not oily;
  Melt profile: 5-10 seconds after contact with the skin;
  On skin: enough play time for massage; and
  After feel: non-greasy moisture.
Ideally, the product could be adapted slightly depending on desired use and would thus:
  permit different melt profiles.
It is desired that the product also:
  be of low cost;
  remain stable at room temperature; and
  be able to be of desired size, shape and format.

The present invention, which meets these requirements, is a solid cosmetic product which may be used as a massage bar. The present invention can also be used as a source of moisturization of its user.

SUMMARY OF THE INVENTION

The present invention is directed to a melting massage bar that has a unique moisture format that blends butters, oil(s) and fatty alcohol(s) to provide a unique massage experience without the mess of a typical oil and without the "cold" feeling of a regular lotion. The bar starts out solid and melts when warmed by gentle touch, so that caregivers can lovingly massage their baby with a luxuriously soft feeling.

Traditional lotions include application of water to hydrate the skin barrier. The present invention, in contrast, could potentially incorporate into the skin barrier lipid matrix, which is composed of various lipids like ceramides cholesterols, and free fatty acids, to uphold its integrity.

The melting massage bar, which melts into a soothing moisturizer with skin temperature, can also be used to replenish and rejuvenate a user's skin.

The melting massage bar, which melts into a soothing moisturizer with skin temperature, can also be used to moisturize a user's skin.

The melting massage bar, which requires minimal packaging, also helps meet sustainability commitments.

According to a first aspect of the present invention there is provided a personal care product comprising:
  a solid butter;
  a semi-solid butter;
  an oil; and
  a fatty alcohol.

The personal care product of the present invention may also comprise one or more cosmetically acceptable additives. One skilled in the art would know cosmetically acceptable additives that are suitable for incorporation into such compositions. For example, natural actives, binders, colorants, extracts, fillers, fragrances, opacifiers, and mixtures thereof, may be used.

According to another aspect of the present invention there is provided a method of manufacturing a personal care product comprising:
  1. Add solid butter and fatty alcohol to a beaker;
  2. Mix and heat until uniform liquid solution;
  3. Turn off heat.
  4. Add semi-solid butter and oil to beaker.
  5. Mix at high speed for 1-2 minutes.
  6. Pour mixture into mold and flash freeze for about 2 hours.

7. Remove molds from freezer and calibrate to room temperature.

The inventors determined that, in addition to particular combinations and particular amounts of ingredients, flash freezing resulted in a product having the desired traits.

The disclosure may best be understood by reference to the following description taken in conjunction with the accompanying FIGURES, which illustrate particular embodiments.

BRIEF DESCRIPTION OF THE DRAWINGS

FIG. 1 shows different size melting massage bars tested by consumers for size preference data.

DETAILED DESCRIPTION OF THE INVENTION

Definitions

A "butter" includes oils extracted from a natural source that are often used as an emollients.

A "fatty alcohol" is a straight-chain primary alcohol that is derived from natural fats and oils. Examples include cetyl alcohol and behenyl alcohol. Additional examples appear in Table 1 below.

Preferred fatty alcohols are listed below:

| Fatty Alcohol | Carbon Chain Length | Melting Point |
|---|---|---|
| cetyl alcohol | 16 | 49° C. |
| behenyl alcohol | 22 | 70° C. |
| cetearyl alcohol | blend of cetyl (16) and stearyl (18) | 50° C. |
| stearyl alcohol | 18 | 59° C. |
| olely alcohol | 18 (double bond) | 13-19° C. |
| decyl alcohol | 10 | 6.4° C. |
| isostearyl alcohol | 18 (branched) | 0° C. |
| lauryl alcohol | 12 | 24° C. |
| myristyl alcohol | 14 | 38° C. |
| arachidyl alcohol | 20 | 65° C. |

"Flash freezing" is the process of freezing an item quickly at an extremely low temperature.

An "oil" is a substance that at ambient temperature is a viscous, flowable liquid and has both hydrophobic and lipophilic properties. An example of an oil is *Helianthus annuus* (sunflower) seed oil.

An example of an oil is sunflower seed oil, which is defined according to the ratios of its fatty acid components: linoleic acid constitutes approximately 60% of the oil, which also contains oleic acid, palmitic acid, stearic acid, and linolenic acid. Linoleic acid has been shown to be a necessary fatty acid to maintain normal barrier function of the epidermis.

A "semi-solid" is a substance that at ambient temperature is in a state between a solid and a liquid; it conforms to a

TABLE 1

| Name | Carbon Atoms | Branches/Saturation | Formula |
|---|---|---|---|
| tert-Butyl alcohol | 4 carbon atoms | branched | C4H10O |
| tert-Amyl alcohol | 5 carton atoms | branched | C5H12O |
| 3-Methyl-3-pentanol | 6 carton atoms | branched | C6H14O |
| 1-Heptanol (enanthic alcohol) | 7 carton atoms | | C7H16O |
| 1-Octanol (capryl alcohol) | 8 carbon atoms | | C8H18O |
| Pelargonic alcohol (1-nonarol) | 9 carbon atoms | | C9CH20O |
| 1-Decanol (decyl alcohol, capric alcohol) | 10 carbon atoms | | C10H22O |
| Undecyl alcohol (1-undercanol, undecanol, Hendecanol) | 11 carbon atoms | | C11H24O |
| Lauryl alcohol (dodecanol, 1-dodecanol) | 12 carbon atoms | | C12H26O |
| Tridecyl alcohol (1-tridecanol, tridecanol, Isotridecanol) | 13 carbon atoms | | C13H28O |
| Myristyl alcohol (1-tetradecanol) | 14 carbon atoms | | C14H30O |
| Pentadecyl alcohol (1-pentadecanol, pentdecanol) | 15 carbon atoms | | C15H32O |
| Cetyl alcohol (1-hexadecanol) | 16 carbon atoms | | C16H34O |
| Palmitoleyl alcohol (cis-9-hexadecen-1-ol) | 16 carbon atoms | unsaturated | C16H32O |
| Heptadecyl alcohol (1-n-heptadecanol, heptadecanol) | 17 carbon atoms | | C17H36O |
| Stearyl alcohol (1-octadecanol) | 18 carbon atoms | | C18H38O |
| Oleyl alcohol (1-octadecenol) | 18 carbon atoms | unsaturated | C18H38O |
| Nonadecyl alcohol (1-nonadecanol) | 19 carbon atoms | | C19H40O |
| Arachidyl alcohol (1-eicosanol) | 20 carbon atoms | | C20H42O |
| Henelcosyl alcohol (1-henelcosanol)) | 21 carbon atoms | | C21H44O |
| Behenyl alcohol (1-docosanol) | 22 carbon atoms | | C22H46O |
| Erucyl alcohol (cis-13-doccsen-1-ol) | 22 carbon atoms | unsaturated | C22H50O |
| Lignoceryl alcohol (1-tetracosanol) | 24 carbon atoms | | C24H44O |
| Ceryl alcohol (1-hexacosanol) | 26 carbon atoms | | C26H54O |
| 1-Heptacosanol | 27 carbon atoms | | C27H56O |
| Montanyl alcohol, cluytyl alcohol, or 1-octacosanol | 28 carbon atoms | | C28H58O |
| 1-Nonacosanol | 29 carbon atoms | | C29H60O |
| Myricyl alcohol, mellssyl alcohol, or 1-triacontanol | 30 carbon atoms | | C30H62O |
| 1-Dotriacontanol (Lacceryl alcohol) | 32 carbon atoms | | C32H66O |
| Geddyl alcohol (1-tetratriacontanol) | 34 carbon atoms | | C34H70O | shape when pressure is applied to it; and it has the ability to flow under pressure (e.g., it is spreadable). An example of a semi-solid is *Butyrospermum parkii* (shea) butter, a "semi-solid butter".

A "solid" is a substance that at ambient temperature has structural rigidity and does not change shape or volume; and is not liquid or fluid. An example of a solid is *Theobroma Cacao* (cocoa) seed butter, a "solid butter".

A "wax" is a complex mixtures of alcohols, fatty acids and esters. It is harder, less greasy and more brittle than fats, and are very resistant to moisture, oxidation and microbial degradation.

Examples of waxes include beeswax, candelilla, carnauba and polyethylene waxes.

Embodiments of the present invention will now be described by way of example.

EXAMPLES

Examples 28A and 28B

| Ingredient | Amount (wt %) |
|---|---|
| Beaker A | |
| White cocoa butter | 70 |
| Shea butter | 20 |
| Rice wax | 2.5 |
| Sunflower oil | 7.5 |
| Total | 100 |
| Beaker B | |
| White cocoa butter | 70 |
| Shea butter | 20 |
| Beeswax | 2.5 |
| Sunflower oil | 7.5 |
| Total | 100 |

1. Add white cocoa butter and rice wax to beaker A. Add white cocoa butter and beeswax to beaker B.
2. Add heat to both beakers and mix.
3. After each solution is uniformly mixed and melted, turn off heat.
4. Add shea butter and sunflower oil to each beaker.
5. Mix at high speeds for 2 minutes.
6. Pour mixtures into molds, flash freeze. (Samples remained in the freezer for 2 days).

Observations
  Bar A—In hand, was dry and strong, bar did not compress under pressure. When applied to skin, bar applied like a light balm. Very moisturizing after feel.
  Bar B—In hand, was dry and very strong, bar did not compress under pressure. When warmed in hands, a light oil was applied to skin and was spreadable. Moisturizing after feel.

Although these formulas meet the aesthetic requirements, they would be too expensive to manufacture/sell due to the high level of cocoa butter.

Examples 42A and 42B

A—Attempt to decrease formula cost by decreasing percent weight of cocoa butter. Structural agent here is beeswax.
B—Attempt to decrease formula cost by decreasing percent weight of cocoa butter. Structural agent here is beeswax and cetyl alcohol.

| Ingredient | Amount (wt %) |
|---|---|
| Beaker A | |
| White cocoa butter | 60 |
| Shea butter | 20 |
| Sunflower oil | 10 |
| Beeswax | 10 |
| Total | 100 |
| Beaker B | |
| White cocoa butter | 60 |
| Shea butter | 20 |
| Sunflower oil | 10 |
| Beeswax | 5 |
| Cetyl alcohol | 5 |
| Total | 100 |

1. Add white cocoa butter and beeswax to beakers A and B. Add cetyl alcohol to beaker B.
2. Add heat to both beakers.
3. Once materials are melted, add shea butter.
4. Mix until liquid homogeneous solution.
5. Add sunflower oil.
6. Mix at high speeds for 1 minute. Turn off, stir immediately.
7. Pour mixtures into molds, flash freeze for 2 hours.

Observations
  Both structures cracked when being removed from molds. Structures were too weak to assess.

Examples 43A and 43B

| Ingredient | Amount (wt %) |
|---|---|
| Beaker A | |
| White cocoa butter | 65 |
| Shea butter | 15 |
| Sunflower oil | 10 |
| Cetyl alcohol | 10 |
| Total | 100 |
| Beaker B | |
| White cocoa butter | 60 |
| Shea butter | 15 |
| Sunflower oil | 10 |
| Cetyl alcohol | 15 |
| Total | 100 |

1. Add white cocoa butter and cetyl alcohol to beakers A and B.
2. Add heat to both beakers.
3. Add shea butter.
4. Heat and mix until uniform liquid mixtures.
5. Add sunflower oil.
6. Mix at high speeds for 1 minute. Turn off, stir immediately.
7. Pour mixtures into molds, flash freeze for 2 hours. (left in freezer for 18 hours; ice shadings formed and fell into molds)

Observations
  A—In hand study, slight melt in hand; melted very quickly on application; bar started to slip in hand; structure very strong.
  B—Bar to oil; melts quickly on skin but not too melty in hand; very spreadable oil; feels light and moisturizing; structure very strong.

This example shows that the structure could hold up with solely cetyl alcohol in the formula.

Example 44

| Ingredient | Amount (wt %) |
|---|---|
| White cocoa butter | 60 |
| Shea butter | 15 |
| Sunflower oil | 5 |
| Cetyl alcohol | 20 |
| Total | 100 |

1. Add white cocoa butter and cetyl alcohol to beaker.
2. Heat and mix until uniform liquid solution.
3. Add shea butter. Turn off heat.
4. Add sunflower oil. Immediately pour mixture into molds. Flash freeze for 2 hours.
5. Remove molds from freezer and calibrate to room temperature.

Observations

In hand, not melty, dry, smooth. On application, melts quickly, residue is a thick oil, but not too oily. After feel is very soft and moisturizing.

Increased cetyl alcohol still upheld the structure of the bar and created a "creamy"/"moisturizing" feel to the product.

Example 47

| Ingredient | Amount (wt %) |
|---|---|
| White cocoa butter | 60 |
| Shea butter | 15 |
| Sunflower oil | 10 |
| Beeswax | 15 |
| Total | 100 |

1. Add white cocoa butter and beeswax to beaker.
2. Heat and mix until uniform liquid solution.
3. Add shea butter. Mix until uniform liquid solution. Turn off heat.
4. Add sunflower oil. Mix at high speeds for 1 minute. Immediately pour mixture into molds. Flash freeze for 2 hours.
5. Remove molds from freezer and calibrate to room temperature.

Observations

Bar cracked in molds. Unable to evaluate.

Incorporating beeswax as a structuring agent in amounts similar to the amounts of cetyl alcohol resulted in a prototype that did not maintain structure.

Example 58

| Ingredient | Amount (wt %) |
|---|---|
| White cocoa butter | 60 |
| Behenyl alcohol | 20 |
| Shea butter | 15 |
| Sunflower oil | 5 |
| Total | 100 |

1. Add white cocoa butter and behenyl alcohol to beaker.
2. Add heat.
3. Once mixture is melted, turn off heat and add shea butter.
4. Mix until uniform liquid solution.
5. Add sunflower oil. Mix at high speeds for 1 minute. Immediately pour mixture into molds. Flash freeze.

Observations

Structure was very strong. No fracturing with pressure in hand. The bar was dry, smooth. On skin, it melted slowly, bar to light oil; very glossy; almost balmy. Skin felt very moisturized after application.

Behenyl alcohol is another member of the fatty alcohol family. This formula had great structure and still felt creamy and moisturizing n the skin.

Example 59

| Ingredient | Amount (wt %) |
|---|---|
| White cocoa butter | 60 |
| Ceteareth-20, cetearyl alcohol | 20 |
| Shea butter | 15 |
| Sunflower oil | 5 |
| Total | 100 |

1. Add white cocoa butter and ceteareth-20, cetearyl alcohol to beaker.
2. Add heat.
3. Once mixture is melted, turn off heat and add shea butter.
4. Mix until uniform liquid solution.
5. Add sunflower oil. Mix at high speeds for 1 minute. Immediately pour mixture into molds. Flash freeze.

Observations

Structure in hand felt strong, no fracturing under pressure. Bar was glossy, shiny. Bar melted slowly upon application. Bar melted to light oil/balm. Skin felt very moisturized after skin application.

Formulation with the blend ceteareth-20, cetearyl alcohol this formulation still upheld structure and maintained the creamy, moisturizing aesthetic.

Summary of Results

Formulations were tested to determine acceptability. Results are presented in Table 2 below, wherein (+) denotes acceptable; (−) denotes not acceptable.

TABLE 2

| Sample No. | Ingredients (%) | Feel in Hand | Melt Time | Skin Apn | Aft Feel | Struct | Price |
|---|---|---|---|---|---|---|---|
| 5 | Cocoa (43%) Shea (22%) Canola (20%) Candella (15%) | + | + | + | + | − | + |
| 17B | Shea (30%) Kokum (10%) Coconut (40%) Candella (5%) Bees (15%) | + | + | − | − | + | + |
| 18B | Shea (10%) Kokum (30%) Coconut (40%) Candella (5%) Bees (15%) | − | + | − | − | − | + |
| 22B | Cocoa (50%) Shea (20%) Mango (5%) Coconut (10%) Candella (15%) | + | − | − | + | + | − |
| 28A | Cocoa (70%) Shea (20%) | + | + | + | + | + | − |

TABLE 2-continued

| Sample No. | Ingredients (%) | Feel in Hand | Melt Time | Skin Apn | Aft Feel | Struct | Price |
|---|---|---|---|---|---|---|---|
| | Sunflower oil (7.5%) Rice wax (2.5%) | | | | | | |
| 28B | Cocoa (70%) Shea (20%) Sunflower (7.5%) Bees (2.5%) | + | + | + | + | + | − |
| 42A | Cocoa (60%) Shea (23%) Sunflower oil (11.5%) Beeswax (5.5%) | Unable to evaluate | Unable to evaluate | Unable to evaluate | Unable to evaluate | − | + |
| 42B | Cocoa (60%) Shea (20%) Sunflower oil (10%) Beeswax (5%) Cetyl alcohol (5%) | Unable to evaluate | Unable to evaluate | Unable to evaluate | Unable to evaluate | − | + |
| 43A | Cocoa (65%) Shea (15%) Sunflower oil (10%) Cetyl alcohol (10%) | + | − | + | + | + | + |
| 43B | Cocoa (60%) Shea (15%) Sunflower oil (10%) Cetyl alcohol (15%) | + | + | + | + | + | + |
| 44 | Cocoa (60%) Shea (15%) Sunflower oil (5%) Cetyl alcohol (20%) | + | + | + | + | + | + |
| 47 | Cocoa (60%) Shea (15%) Sunflower oil (10%) Beeswax (15%) | Unable to evaluate | Unable to evaluate | Unable to evaluate | Unable to evaluate | Unable to evaluate | + |
| 58 | Cocoa (60%) Shea butter (15%) Sunflower oil (5%) Behenyl alcohol (20%) | + | + | + | + | + | + |
| 59[1] | Cocoa (60%) Shea butter (15%) Sunflower oil (5%) Ceteareth-20, ceteryl alcohol (20%) | + | + | + | + | + | + |

For ease of reference, a summary of the "type" of ingredients in the formulas tested is presented in Table 3 below.

TABLE 3

| | A | B | | | C | D | | E | |
|---|---|---|---|---|---|---|---|---|---|
| INCI Name | Synthetic Beeswax | Candelilla Wax | Behenyl Alcohol | Cetearyl Alcohol | Cetyl Alcohol | Kokum butter | Cocoa Butter | White Cocoa Butter | Shea Butter | Coconut Oil | Sunflower Oil |

*A—wax, B—fatty alcohol, C—solid butter, D—semi solid butter, E—oil
*all numbers are weight percent Ratios of the various types of ingredients and associated results are presented in Table 4 below.

TABLE 4

| Formula Number | A:B:C:D:E Ratios | % Fatty Alcohol |
|---|---|---|
| 22B | 0:0:80:15:5 | 0 |
| 28B | 2.5:0:70:20:7.5 | 2.5 |
| 42A | 5.5:0:60:23:11.5 | 0 |
| 42B | 5:5:60:20:5 | 5 |
| 43A | 0:10:65:15:10 | 10 |
| 43B | 0:15:60:15:10 | 15 |
| 44 | 0:20:60:15:5 | 20 |
| 47 | 15:0:60:15:10 | 0 |
| 58 | 0:20:60:15:5 | 20 |
| 59 | 0:20:60:15:5 | 20 |

The following Examples were employed in a consumer use study to determine preference of form.

Prototype 1: Bar to Cream Module
Example 44

| Trade Name | INCI | % w/w |
|---|---|---|
| SMA Cocoa Butter | Theobroma Cacao (Cocoa) Seed Butter | 60 |
| Lanette 16 | Cetyl Alcohol | 0 |
| Biochemica Shea Butter Refined | Butyrospermum Parkii (Shea) Butter | 15 |
| Sunflower Oil Refined | Helianthus Annuus (Sunflower) Seed Oil | 5 |
| | TOTAL: | 100 |

Prototype 2: Bar to Oil Module
Example 43B

| Trade Name | INCI | % w/w |
|---|---|---|
| SMA Cocoa Butter | Theobroma Cacao (Cocoa) Seed Butter | 60 |
| Lanette 16 | Cetyl Alcohol | 15 |
| Biochemica Shea Butter Refined | Butyrospermum Parkii (Shea) Butter | 15 |
| Sunflower Oil Refined | Helianthus Annuus (Sunflower) Seed Oil | 10 |
| | TOTAL: | 100 |

Prototype 3: Bar to Balm Module
Example 94C

| | | |
|---|---|---|
| SMA Cocoa Butter | Theobroma Cacao (Cocoa) Seed Butter | 55 |

-continued

Prototype 3: Bar to Balm Module
Example 94C

| Lanette 16 | Cetyl Alcohol | 20 |
| Biochemica Shea Butter Refined | *Butyrospermum Parkii* (Shea) Butter | 10 |
| Synthetic Beeswax Pastilles SP-772P | Synthetic Beeswax | 7.5 |
| Sunflower Oil Refined | *Helianthus Annuus* (Sunflower) Seed Oil | 7.5 |
| | TOTAL: | 100 |

Preferably, the personal care composition comprises:
cocoa butter;
shea butter;
sunflower oil; and
cetyl alcohol.

Depending on desired traits, the personal care composition may comprise the following ingredients (Example 44):
60% cocoa butter;
15% shea butter;
5% sunflower oil; and
20% cetyl alcohol.
Results in a "butter to cream" type formula.

The personal care composition may also comprise the following ingredients (Example 43A):
65% cocoa butter;
15% shea butter;
10% sunflower oil; and
10% cetyl alcohol.
Results in a Butter to oil type formula.

It will be understood that, while various aspects of the present disclosure have been illustrated and described by way of example, the invention claimed herein is not limited thereto, but may be otherwise variously embodied according to the scope of the claims presented in this and/or any derivative patent application.

REFERENCES (1) 16 Jan. 2019, Society of Cosmetic Chemists. "What Is the Stratum Corneum and Its Importance in Skin Care?" Cosmetics Business, 2016, www.cosmeticsbusiness.com/news/article_page/What_is_the_stratum_corneum_and_its_importance_in_skin_care/143839.
(2) "Clean Beauty." Google Trends, Google, trends.google.com/trends/?geo=US.
(3) Gunstone, F. D. Fatty Acid and Lipid Chemistry. Springer, 2012.
(4) "How to Take Care of Your Skin: Understanding the Skin Barrier." AYR SKIN CARE, ayrskincare.com/blog/how-to-take-care-of-your-skin-understanding-the-skin-barrier/.
(5) Lencki, Robert W., and R. John Craven. "Negative Pressure Induced Cavity Formation During Cocoa Butter Crystallization." SpringerLink, Springer Berlin Heidelberg, 3 Jul. 2013, link.springer.com/article/10.1007%2Fs11746-013-2294-0.
(6) Karagounis et al., Use of "natural" oils for moisturization: Review of olive, coconut, and sunflower seed oil, Pediatric Dermatology, 2019; 36:9-15
(7) Lin et al., Anti-Inflammatory and Skin Barrier Repair Effects of Topical Application of Some Plant Oils, Int. J. Mol. Sci. 2018, 19, 70.
(8) Cizinauskas et al., Fatty acids penetration into human skin ex vivo: ATOF-SIMS analysis approach, Biointerphases 12(1), March 2017.

What is claimed is:

1. A personal care cosmetic composition comprising:
about 60% to about 65% of a solid butter;
about 15% of a semi-solid butter, wherein the semi-solid butter is provided in a lesser weight percent of the personal care cosmetic composition than the solid butter;
an oil; and
about 10% to about 20% of a fatty alcohol, wherein the fatty alcohol is selected from the group consisting of the fatty alcohols listed in the table below:

| Name |
| --- |
| tert-Butyl alcohol |
| tert-Amyl alcohol |
| 3-Methyl-3-pentanol |
| 1-Heptanol (ethanthic alcohol) |
| 1-Octanol (capryl alcohol) |
| Pelargoic alcohol (1-nonanol) |
| 1-Decanol (decyl alcohol, capric alcohol) |
| Undecyl alcohol (1-undecanol, decanol, Hendecanol) |
| Lauryl alcohol (dodecanol, 1-dodecanol) |
| Tridecyl alcohol (1-tridecanol, tridecanol, isotridecanol) |
| Myristyl alcohol (1-tetradecanol) |
| Pentadecyl alcohol (1-pentadecanol, pentadecanol) |
| Cetyl alcohol (1-hexadecanol) |
| Palmitoleyl alcohol (6-9-hexadecen-1-ol) |
| Heptadecyl alcohol (1-n-heptadecanol, heptadecanol) |
| Stearyl alcohol (1-octadecanol) |
| Oleyl alcohol (1-octadecenol) |
| Nonadecyl alcohol (1-nonadecanol) |
| Arachidyl alcohol (1-eicosanol) |
| Heneicosyl alcohol (1-heneicosanol) |
| Behenyl alcohol (1-docosanol) |
| Erucyl alcohol (cis-13-docosen-1-ol) |
| Lignoceryl alcohol (1-tetracosanol) |
| Ceryl alcohol (1-hexacosanol) |
| 1-Heptacosanol |
| Montanyl alcohol, cluytyl alcohol, or 1-octacosanol |
| 1-Nonacosanol |
| Myricyl alcohol, melissyl alcohol, or 1-triacontanol |
| 1-Dotriacontanol (Lacceryl alcohol) |
| Geddyl alcohol (1-tetratriacontanol). |

2. The personal care cosmetic composition of claim 1, wherein the personal care composition is solid at room temperature.

3. The personal care cosmetic composition of claim 1, further comprising at least one additional component selected from the group consisting of natural actives, binders, colorants, extracts, fillers, fragrances, opacifiers, and mixtures thereof.

4. The personal care cosmetic composition of claim 1, wherein the personal care composition is employed as a massage bar.

5. A method comprising contacting the skin of a user with the personal care cosmetic composition of claim 1.

6. The method of claim 5, wherein the method is employed to massage the user.

7. The method of claim 5, wherein the method is employed to moisturize the user's skin.

8. The method of claim 5, wherein the method is employed to replenish and rejuvenate the user's skin.

9. The personal care cosmetic composition of claim 1, wherein the fatty alcohol is selected from one or more of the group consisting of cetyl alcohol; behenyl alcohol; stearyl alcohol; oleyl alcohol; decyl alcohol; isostearyl alcohol; lauryl alcohol; myristyl alcohol; and arachidyl alcohol.

* * * * *